(12) United States Patent
Pepys

(10) Patent No.: US 7,045,499 B2
(45) Date of Patent: May 16, 2006

(54) THERAPEUTIC AGENT

(75) Inventor: Mark Pepys, London (GB)

(73) Assignee: Pentraxin Therpeutics Limited, London (GB)

( * ) Notice: Subject to any disclaimer, the term of this patent is extended or adjusted under 35 U.S.C. 154(b) by 0 days.

(21) Appl. No.: 09/985,699

(22) Filed: Nov. 5, 2001

(65) Prior Publication Data
US 2006/0014665 A1 Jan. 19, 2006

(30) Foreign Application Priority Data
Aug. 8, 2001 (GB) .................................... 0119370

(51) Int. Cl.
A01N 37/18 (2006.01)
(52) U.S. Cl. ........................................................ 514/2
(58) Field of Classification Search .................. 514/422
See application file for complete search history.

(56) References Cited

U.S. PATENT DOCUMENTS 4,783,480 A * 11/1988 Wakatsuka et al.
4,895,872 A * 1/1990 Nitecki et al.
6,103,910 A * 8/2000 Hertel et al.
6,365,570 B1 * 4/2002 Van Kessel et al. ............. 514/8

FOREIGN PATENT DOCUMENTS

EP 0915088 5/1999
WO WO 9746098 12/1997
WO WO 98/50420 * 11/1998

OTHER PUBLICATIONS

Iverson, "Amyloid diseases: Small drugs lead the attack," Nature, p. 414: 231-233, (2002).
Borman, "Chemistry Highlights 2002, Medicinal and Combinatorial Chemistry," Chem. Eng. News, p. 80: 37-38, (2002).
PCT search report PCT/GB 02/03504.
Lindorfer et al., "A bispecific dsDNAXmonoclonal antibody construct for clearance af anti-dsDNA IGG in systemic lupus erythematosus", J. Immunol. Methods 248, 125-138, 2001.
Riedstra et al., "Study of an anti-human transthyretin immunoadsorbent—influence of coupling chemistry on binding capacity and ligand leakage", J. Chromatogr. B: Biomedical Sciences & Applications. 705(2), 213-222, 1998.
Paul et al., "Identification of optimal anion spacing for anti-HIV activity in a series of cosalane tetracarboxylates", Bioorg. Med. Chem. Lett. 10(18), 2149-2152, 2000.
Cleaveland et al., "Site of action of two novel pyrimidine biosynthesis inhibitors accurately predicted by the compare program", Biochem. Pharmacol. 49(7), 947-954, 1995.

Purkey et al., "Evaluating the binding selectivity of transthyretin amyloid fibril inhibitors in blood plasma", Proc. Natl. Acad. Sci. USA 98(10), 5566-5571, 2001.
Pepys et al., "Targeted pharmacological depletion of serum amyloid P component for treatment of human amyloidosis", Nature 417, 254-259, 2002.
Hind et al., "Specific chemical dissociation of fibrillar and non-fibrillar components of amyloid deposits", Lancet, 376-378, 1984.
Tennent et al., "Serum amyloid P component prevents proteolysis of the amyloid fibrils of Alzheimer disease and systemic amyloidosis", Proc. Natl. Acad. Sci. USA 92, 299-4303, 1995.
Pepys et al., "Molecular mechanisms of fibrillogenesis and the protective role of amyloid P component: two possible avenues for therapy", The Nature and Origin of Amyloid Fibrils, 73-89, 1996.
Pepys et al., "Amyloid P component. A critical review.", Int. J. Exp. Clin. Invest. 4, 274-295, 1997.
Pepys, "C-reactive protein and amyloidosis: from protein to drugs?", The Lumleian Lecture, 397-414.
Nelson et al., "Serum amyloid P component in chronic renal failure and dialysis", Clinica Chimica Acta 200, 191-200, 1991.
Booth et al., "Instability, unfolding and aggregation of human lysozyme variants underlying amyloid fibrillogenesis", Nature 385, 787-793, 1997.
Pepys et al., "Human lysozyme gene mutations cause hereditary systemic amyloidosis", Nature 362, 553-557, 1993.
Holmgren et al., Biochemical effect of liver transplantation in two Swedish patients with familial amyloidotic polyneuropathy (FAP-met$^{30}$), Clin. Genet. 40, 242-246, 1991.
Pepys et al., "Isolation of amyloid P component (Protein AP) from normal serum as a calcium-dependent binding protein", Lancet, 1029-1031, 1977.
Pontet et al., "One step preparation of both human C-creative protein and Cit", FEBS Letters 88(2), 172-175, 1978.
Hind et al., "Binding specificity of serum amyloid P component for the pyruvate acetal of galactose", J. Exp. Med. 159, 1058-1069, 1984.
Emsley et al., "Structure of pentameric human serum amyloid P component", Nature 367, 338-345, 1994.

(Continued)

Primary Examiner—Michael Meller
(74) Attorney, Agent, or Firm—Pillsbury Winthrop Shaw Pittman LLP

(57) ABSTRACT

The invention relates to an agent for the depletion of unwanted proteins from plasma comprising a plurality of ligands covalently co-linked to produce a complex with a plurality of proteins whierein at least two of the ligands are capable of being bound by ligand binding sites on the proteins and wherein the non-protein access agent excludes certain D-proline derivatives.

10 Claims, 10 Drawing Sheets

OTHER PUBLICATIONS

Hohenester et al., "Crystal structure of a decameric complex of human serum amyloid P component with bound dAMP", *J. Mol. Biol.* 269, 570-578, 1997.

Ashton et al., "Pentameric and decameric structures in solution of serum amyloid P component by X-ray and neutron scattering and molecular modelling analyses", *J. Mol. Biol.* 272, 408-422, 1997.

Baltz et al., "Calcium-dependent aggregation of human serum amyloid P component", *Biochim. Biophys. Acta* 701, 229-236, 1982.

Booth et al., "Analysis of autoaggregation and ligand binding sites of serum amyloid P component by in vitro mutagenesis", *Amyloid and Amyloidosis 1998*, 23-25, 1998.

Hutchinson et al., "Human serum amyloid P component is a single uncomplexed pentamer in whole serum", *Mol. Med.* 6(6), 482-493, 2000.

Hawkins et al., "Metabolic studies of radioiodinated serum amyloid P component in normal subjects and patients with systemic amyloidosis", *J. Clin. Invest.* 86, 1862-1869, 1990.

Hutchinson et al., "The petraxins, C-reactive protein and serum amyloid P component, are cleared and catabolized by hepatocytes in vivo", *J. Clin. Invest.* 94, 1390-1396, 1994.

Pepys et al., "Human serum amyloid P component is an invariant constituent of amyloid deposits and has a uniquely homogeneous glycostructure", *Proc. Natl. Acad. Sci. USA* 91, 5602-5606, 1994.

Holmgren et al., "Clinical improvement and amyloid regression after liver transplantation in hereditary transthyretin amyloidosis", *Lancet*, 1113-1116, 1993.

Klabunde et al., "Rational design of potent human transthyretin amyloid disease inhibitors", *Nature Struct. Biol.* 7(4), 312-321, 2000.

Solomon et al., Heterobifunctional Multivalent Inhibitor-Adaptor Medietes Specific Aggregates between Shiga Toxin and a Pentraxin Organic Letters, American Chemical Society, Vol. 7 (No. 20). pp. 4369-4372.

\* cited by examiner

THERAPEUTIC AGENT

The present invention relates to an agent for the depletion of an unwanted protein population from the plasma of a subject, use of the agent for the preparation of a therapeutic composition, and a method for treatment using the agent.

BACKGROUND TO THE INVENTION

Proteins in the blood plasma, in the extracellular matrix of the tissues, and in cells are essential for all vital physiological functions. However, many different proteins also contribute to disease. The underlying pathogenetic mechanisms include overproduction of normal proteins with corresponding excessive effects, the production of abnormal proteins with damaging effects, and the incidental subversion of normal protein function leading to damaging effects during intercurrent pathological processes, such as inflammation and microbial infection. There is therefore a need for elimination of a variety of normal or abnormal proteins from the body to provide treatment for many human diseases. Plasma proteins that contribute to pathogenesis of disease include cytokines, lipoproteins, autoantibodies, components of the complement and coagulation pathways, amyloidogenic proteins including monoclonal immunoglobulin light chains, transthyretin, lysozyme and $\beta_2$-microglobulin, acute phase proteins in particular serum amyloid A protein (SAA), and pentraxins such as serum amyloid P component (SAP). All these different proteins, produced by different cells, are potentially attractive targets for therapeutic elimination in various diseases. However, there are few effective methods for selectively lowering the circulating concentration of specific proteins and those approaches that are available, or have been attempted, are complex, difficult and subject to many extremely challenging problems.

Cytokines are protein hormones produced by and acting on a variety of different cell types, and are critically important mediators of host defence, immunological and inflammatory responses, but their overproduction in some diseases contributes to serious pathology, morbidity and mortality. Antibodies and recombinant binding proteins have lately been used successfully for targeting one particular cytokine, tumor necrosis factor (TNF), and TNF blockade is therapeutically beneficial in rheumatoid arthritis and Crohn's disease, but there are few effective methods for reducing damaging high levels of other cytokines.

Pathogenic overproduction of other normal proteins, such as acute phase plasma proteins, can be reduced by suppressing the activity of an underlying primary disease, but, except in the case of treatable chronic infection, this is usually extremely difficult to achieve. There is no cure for chronic idiopathic inflammatory diseases, such as rheumatoid arthritis or Crohn's disease, or for most malignant neoplasms. Treatment of these diseases and suppression of their activity require regimens including highly toxic anti-inflammatory, cytotoxic and immunosuppressive drugs, and frequently also surgery and/or radiotherapy.

Production of abnormal proteins, whether inherited or acquired as a complication of another primary disease, is also extremely difficult to control. For example, the variant transthyretin and variant fibrinogen molecules responsible for forms of hereditary systemic amyloidosis, can be eliminated from the plasma only by liver transplantation. No such approach is possible with many other hereditary diseases caused by pathogenic variant proteins. Acquired production of abnormal and pathogenic proteins, as in monoclonal gammopathies, can be treated only with powerful cytotoxic drugs or bone marrow transplantation. These procedures incur universal morbidity, and even mortality rates of up 50%, without being uniformly successful.

Another approach has been to remove damaging proteins by extracorporeal absorption, passing blood over more or less selective solid phase media to remove the target protein. This can make a useful contribution to removal of the high concentrations of pro-atherogenic low density lipoprotein in familial hypercholesterolaemia. It has also been attempted, so far unsuccessfully, for removal of two different amyloidogenic proteins: $\beta_2$-microglobulin in patients on chronic haemodialysis for end stage renal failure, and variant transthyretin in patients with familial amyloid polyneuropathy.

In cases where particular proteins produce their pathogenic effects by binding to specific ligand structures in vivo, a possible approach to therapy is the development of drugs to inhibit such binding. For example, the present inventor has proposed such an approach to the treatment of amyloidosis and Alzheimer's disease, targeting the pathogenic binding of serum amyloid P component to amyloid fibrils by administration of low molecular weight molecules that block such binding (1–5) U.S. Pat. No. 6,126,918). The specific binding of SAP to particular ligands containing anionic groups, including carboxylates and phosphates is known (6–10). In the complex of SAP with deoxyadenosine monophosphate (dAMP), there is a dAMP molecule in the calcium-dependent binding site of each protomer in the homopentameric SAP molecule (10). As a result of base stacking, dependent on hydrogen bonding between pairs of dAMP molecules, pairs of SAP pentamers loaded with dAMP assemble face to face to form a decameric protein-ligand complex (10).

The known low molecular weight ligands of SAP, such as phosphoethanolamine and methyl 4,6-O-(1-carboxyethylidene)-$\beta$-D-galactopyranoside (MO$\beta$DG), are only bound with modest affinity of about millimolar. This is poor compared to the typical nanomolar affinities of most drug-protein interactions, and suggests that such compounds would be unlikely to be effective as inhibitors of the pathogenic binding of SAP to its ligands in vivo. There remains a need to provide an effective method for the targeted depletion of an unwanted plasma protein population.

SUMMARY OF THE INVENTION

Accordingly, in a first aspect, the present invention provides an agent for the depletion of an unwanted protein population from the plasma of a subject, which agent comprises a plurality of ligands covalently co-linked so as to form a complex with a plurality of the proteins in the presence thereof, wherein at least two of the ligands are the same or different and are capable of being bound by ligand binding sites present on the proteins, wherein the agent is a non-proteinaceous agent. Agents disclosed in EP-A-0915088 do not form part of this aspect of the invention. EP-A-0915088 discloses D-prolines of the formula

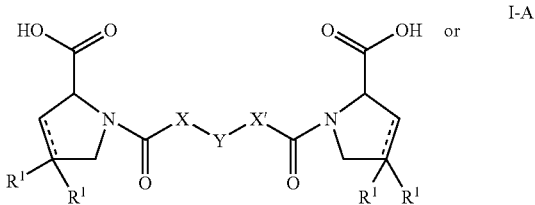

I-A

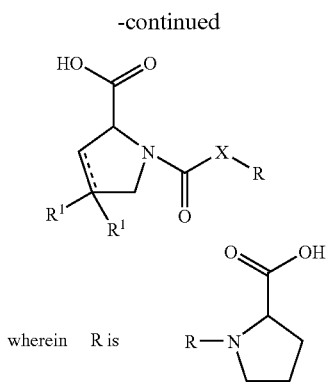

-continued wherein R is the group

R¹ is hydrogen or halogen;

X is —(CH₂)ₙ—; —CH(R²)(CH₂)ₙ—; —CH₂O(CH₂)ₙ—; —CH₂NH—; benzyl, —C(R²)=CH—; —CH₂CH(OH)—; or thiazol-2,5-diyl;

Y is —S—S—; —(CH₂)ₙ—; —O—; —NH—; —N(R²)—; —CH=CH—; —NHC(O)NH—; —N(R²)C(O)N(R²)—; —N[CH₂C₆H₃(OCH₃)₂]—; —N(CH₂C₆H₅)—; —N(CH₂C₆H₅)C(O)N(CH₂C₆H₅)—; —N(alkoxy-alkyl)—; N(cycloalkyl-methyl)—; 2,6-pyridyl; 2,5-furanyl; 2,5-thienyl; 1,2-cyclohexyl; 1,3-cyclohexyl; 1,4-cyclohexyl; 1,2-naphthyl; 1,4-naphthyl; 1,5-naphthyl; 11,6-naphthyl; biphenylen; or 1,2-phenylen, 1,3-phenylen and 1,4-phenylen, wherein the phenylen groups are optionally substituted by 1-4 substituents, selected from halogen, lower alkyl, lower alkoxy, hydroxy, carboxy, —COO-lower alkyl, nitrilo, 5-tetrazol, (2-carboxylic acid pyrrolidin-1-yl)-2-oxo-ethoxy, N-hydroxycarbamimidoyl, 5-oxo[1,2,4]oxadiazolyl, 2-oxo-[1,2,3,5]oxathiadiazolyl, 5-thioxo[1,2,4]oxadiazolyl and 5-tert-butylsulfanyl-[1,2,4]oxadiazolyl;

X' is —(CH₂)ₙ—; —(CH₂)ₙCH(R²)—; —(CH₂)ₙOCH₂—; —NHCH₂—; benzyl, —CH=C(R²)—; —CH(OH)CH₂; or thiazol-2,5-diyl;

R² is lower alkyl, lower alkoxy or benzyl and n is 0-3, and pharmaceutically acceptable salts or mono- or diesters thereof.

Surprisingly, it has been found that agents according to the present invention are dramatically potent in vivo in not only inhibiting ligand binding but also depleting the target protein from the circulation by causing it to be rapidly cleared. The present invention provides a generic method for identification and/or creation of drug molecules that are specifically bound by individual target proteins and then engage the normal, exquisitely sensitive, capacity of the body to recognise and destroy autologous proteins that have undergone changes in conformation or assembly.

Accordingly, there is provided use of a non-proteinaceous agent for the preparation of a composition for the depletion of an unwanted protein population from the plasma of a subject, which agent comprises a plurality of ligands covalently co-linked so as to form a complex with a plurality of the proteins in the presence thereof, wherein at least two of the ligands are the same or different and are capable of being bound by ligand binding sites present on the proteins.

The normal physiological role of each protein depends critically on its appropriate molecular conformation and/or assembly, and the body has powerful mechanisms to detect and destroy proteins that are damaged, aggregated or misfolded. The purpose of the present invention is to specifically target individual proteins and cause them to be identified by the body's own physiological mechanisms as requiring prompt clearance and destruction. In order to achieve this effect the invention advantageously uses palindromic agents that aggregate the proteins as dimers or higher order aggregates.

The exact structure of the agent of the present invention will be dependent upon the protein or proteins of the unwanted protein population targeted according to the invention. In a preferred embodiment, the unwanted population consists essentially of a single protein species which will bear one or, in some cases, more than one ligand binding site. Many proteins are specifically equipped, as part of their normal function, to bind particular low molecular weight ligands. In the simple case where the single protein species has a single ligand binding site, each ligand in the therapeutic agent would be selected to be capable of being bound in that ligand binding site. The ligand could be selected from the ligands known to be bound by that binding site, ligands predicted to be bound by that site perhaps on the basis of structural information available on the binding site such as X-ray crystallographic information, or structural analogues thereof. For target proteins without known low molecular weight ligands, suitable compounds can be identified by high throughput screening of chemical libraries and/or structure based molecular design. The affinity of each individual ligand-protein binding site interaction does not need to be particularly high provided that the ligand is specific for each target protein. It is possible that a dissociation constant of up to 10 millimolar would suffice. However, it is preferred that the dissociation constant is no more than 1 millimolar, more preferably less than 100 micromolar, most preferably less than 10 micromolar. The affinity is preferably about micromolar or higher. Micromolar affinity has been found to be sufficient in the case of SAP, although the highest possible affinity is clearly desirable.

In the agents of the present invention, although the ligands may be directly linked together by a covalent bond, the ligands are preferably covalently co-linked by a linker. This enables the ligands to be sufficiently spatially separated whereby a plurality of target proteins may be bound to the agent without one protein hindering the binding of the other protein or proteins. The exact structure of the linker is not critical although it is typically preferred not to include reactive groups. The linker may comprise a linear or branched hydrocarbylene which may have one or more of its carbon atoms optionally substituted by a heteroatom. The linker may have a chain length in the range 2 to 20 atoms. Useful chain length and chemical composition may be determined empirically depending on the proteins with which the agent is to be complexed. Where the agent has two ligands, the linker is typically linear; a preferred general structure is ligand-linker-ligand. This is conveniently denoted a "palindrome" for the purposes of the present application. Although other structures involving three, four or more ligands with an appropriate branched chain linker are also contemplated where three, four or more target proteins could form a complex.

In a further embodiment, at least two of the ligands in the agent are different from one another and are capable of binding different proteins. In this embodiment, the unwanted protein population consists essentially of two protein species or more. In this way, two different types of protein can be targeted for depletion. It is possible to use a protein known to be rapidly depleted, such as SAP, to enhance the clearance of another target protein by designing the agent with one ligand capable of being bound by SAP and having a second different ligand for targeting the different target protein for clearance with the SAP.

The target protein may be a normal molecule or an abnormal, variant, molecule. The ligand binding site of the agent according to the invention may be from a cytokine, a lipoprotein, an autoantibody, an acute phase protein, an amyloidogenic protein or a component of the complement or coagulation pathway. Where the ligand binding site is from an acute phase protein, this may comprise SAA.

Where the ligand binding site is from an amyloidogenic protein, this may comprise a monoclonal immunoglobulin light chain, $\beta_2$-microglobulin, transthyretin or lysozyme.

Where the ligand binding site is from lysozyme, at least one of the ligands comprises a disaccharide or oligosaccharide analogue containing at least N-acetyl muramic acid linked via its C1 atom to the C4 atom of, for example, N-acetyl glucosamine, with the O atom of the 1,4 β glycosidic linkage replaced by a carbon or other non-O atom.

In the case of SAP, one class of agents comprises the D-prolines of formula set out above, preferably (R)-1-[6-(R)-2-Carboxy-pyrrolidin-1-yl]-6-oxo-hexanoyl] pyrrolidine-2-carboxylic acid or a pharmaceutically acceptable salt or mono- or diester thereof.

The agent may be used to deplete unwanted protein populations from the plasma of human or animal subjects. At appropriate molar ratios of agent to target protein, the agent cross links pairs of protein molecules to produce complexes that are recognised in the body as abnormal and are then promptly cleared and catabolised. This leads to substantial or complete depletion of the target protein and confers therapeutic benefit.

Pharmaceutical compositions may be formulated comprising an agent according to the present invention optionally incorporating a pharmaceutically-acceptable excipient, diluent or carrier. The pharmaceutical compositions may be in the form of a prodrug comprising the agent or a derivative thereof which becomes active only when metabolised by the recipient. The exact nature and quantities of the components of such pharmaceutical compositions may be determined empirically and will depend in part upon the route of administration of the composition. Routes of administration to recipients include oral, buccal, sublingual, by inhalation, topical (including ophthalmic), rectal, vaginal, nasal and parenteral (including intravenous, intra-arterial, intra-muscular, subcutaneous and intraarticular). For convenience of use, dosages according to the present invention are preferably administered orally but this will depend on the actual drug and its bioavailability. A typical dosage will be 50 to 500 mg per day orally or by continuous intravenous infusion, or intermittent subcutaneous injection, for example of (R)-1-[6-(R)-2-Carboxy-pyrrolidin-1-yl]-6-oxo-hexanoyl] pyrrolidine-2-carboxylic acid.

BRIEF DESCRIPTION OF THE INVENTION

The present invention will now be described in further details by way of example only, with reference to the following Examples and to the accompanying drawings, in which.

DETAILED DESCRIPTION OF THE INVENTION

EXAMPLES

Figure 1:
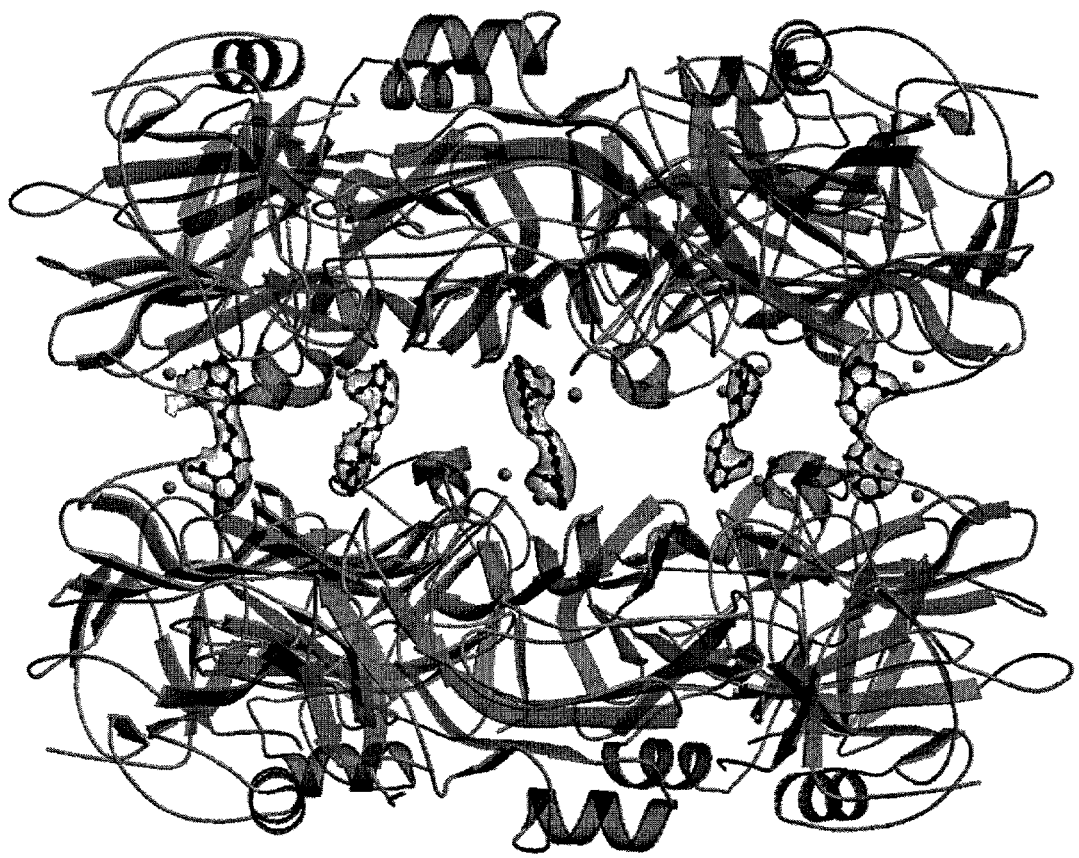
FIG. 1 shows the three dimensional X-ray crystal structure of SAP complexed with an agent of the present invention.

SERUM AMYLOID P COMPONENT AND (R)-1-[6-(R)-2-CARBOXY-PYRROLIDIN-1-YL]-6-OXO-HEXANOYL]PYRROLIDINE-2-CARBOXYLIC ACID

A method for screening and testing inhibitors of serum amyloid P component (SAP) binding to amyloid fibrils in vitro was devised and used in collaboration with F Hoffmann-La Roche Ltd to identify a suitable lead molecule for drug development. A library of candidate compounds was screened accordingly. The subsequent collaborative medicinal chemistry programme led to synthesis of a family of dicarboxylic acid, pyrrolidone ring containing molecules, of which the most studied is (R)-1-[6-(R)-2-Carboxy-pyrrolidin-1-yl]-6-oxo-hexanoyl]pyrrolidine-2-carboxylic acid. This molecule and related compounds (EP-A-0915088) are modestly potent inhibitors of SAP binding to amyloid fibrils in vitro, with $IC_{50}$ values around 0.5–1.0 µM. However they are all more potent inhibitors than the original lead compound, which was 1-(3-Mercapto-2-methyl-1-oxopropyl)-D-proline, containing just a single D-proline ring and carboxylate.

SAP is a pentamer with 5 identical non-covalently associated protomers each bearing a single calcium dependent ligand binding site on one planar face, the binding (B) face, of the molecule (9). In the absence of calcium, human SAP forms stable decameric dimers, probably via A-face to A-face interactions (11). In the presence of calcium, isolated human SAP rapidly aggregates and precipitates, as a result of molecular lattice formation due to binding of the exposed carboxylate of the Glu167 residue on one SAP molecule by the calcium dependent ligand binding site of another SAP molecule (12,13). This autoaggregation of SAP is inhibited by other ligands to which SAP binds, and all the present inhibitors of SAP binding to amyloid fibrils were active in this respect. However we show here that the greater potency of (R)-1-[6-(R)-2-Carboxy-pyrrolidin-]-yl]-6-oxo-hexanoyl]pyrrolidine-2-carboxylic acid and related compounds, as inhibitors of SAP binding to amyloid fibrils in vitro, results from their capacity to cross link pairs of SAP molecules. The palindromic structure of (R)-1-[6-(R)-2-Carboxy-pyrrolidin-1-yl]-6-oxo-hexanoyl]pyrrolidine-2-carboxylic acid enables it to not only block the ligand binding sites on individual SAP protomers, but could also cross link pairs of pentameric SAP molecules to form B—B face to face decameric dimers. Gel filtration analysis of mixtures of isolated SAP with (R)-1-[6-(R)-2-Carboxy-pyrrolidin-1-yl]-6-oxo-hexanoyl]pyrrolidine-2-carboxylic acid, at ratios between equimolar and 100 fold molar excess of drug (molecular weight 340 Da) to SAP protomers (25,462 Da), show that all the SAP is decameric (Table 1). However at 128 fold or greater molar excess of drug, all the SAP elutes in a volume corresponding to its single pentameric form, because each binding site is then occupied by a different individual (R)-1-[6-(R)-2-Carboxy-pyrrolidin-1-yl]-6-oxo-hexanoyl]pyrrolidine-2-carboxylic acid molecule, preventing cross linking and dimerisation.

TABLE 1

Molecular assembly of isolated pure SAP in the presence of (R)-1-[6-(R)-2-Carboxy-pyrrolidin-1-yl]-6-oxo-hexanoyl]pyrrolidine-2-carboxylic acid in vitro

| Drug:protein molar ratio | Calcium present | Protein | Elution volume (ml) | Molecular assembly |
|---|---|---|---|---|
| No drug | − | CRP | 12.28 | Pentamer |
| No drug | + | CRP | 12.81 | Pentamer |
| 1:1 | + | CRP | 12.58 | Pentamer |
| 10:1 | + | CRP | 11.96 | Pentamer |
| No drug | − | SAP | 10.93 | Decamer |
| 1:1 | + | SAP | 10.97 | Decamer |
| 10:1 | + | SAP | 10.97 | Decamer |
| 128:1 | + | SAP | 12.55 | Pentamer |

C-reactive protein (CRP) is a pentraxin closely related to SAP. Samples of isolated pure human SAP or CRP were mixed with (R)-1-[6-(R)-2-Carboxy-pyrrolidin-1-yl]-6-oxo-hexanoyl]pyrrolidine-2-carboxylic acid at the molar ratios shown, with respect to pentraxin protomer, in physiological ionic strength Tris buffered saline pH 8.0, and analysed by size exclusion chromatography precisely as described previously (14). The mixtures and the column eluants contained either no calcium ions or 2 mM calcium, and the concentrations of drug appropriate to maintain the molar ratios indicated above. In the absence of a specific ligand to which it can bind, purified human SAP is insoluble in the presence of calcium and elutes as high molecular weight aggregates in the void volume of the column (14). However in the absence of calcium and ligand, isolated SAP alone forms stable decamers, providing an excellent marker for the elution volume of this molecular assembly (14). Human CRP is a stable pentamer either in the presence or absence of calcium and thus provides a robust marker for the elution position of that molecular form (14).

Figure 2A:
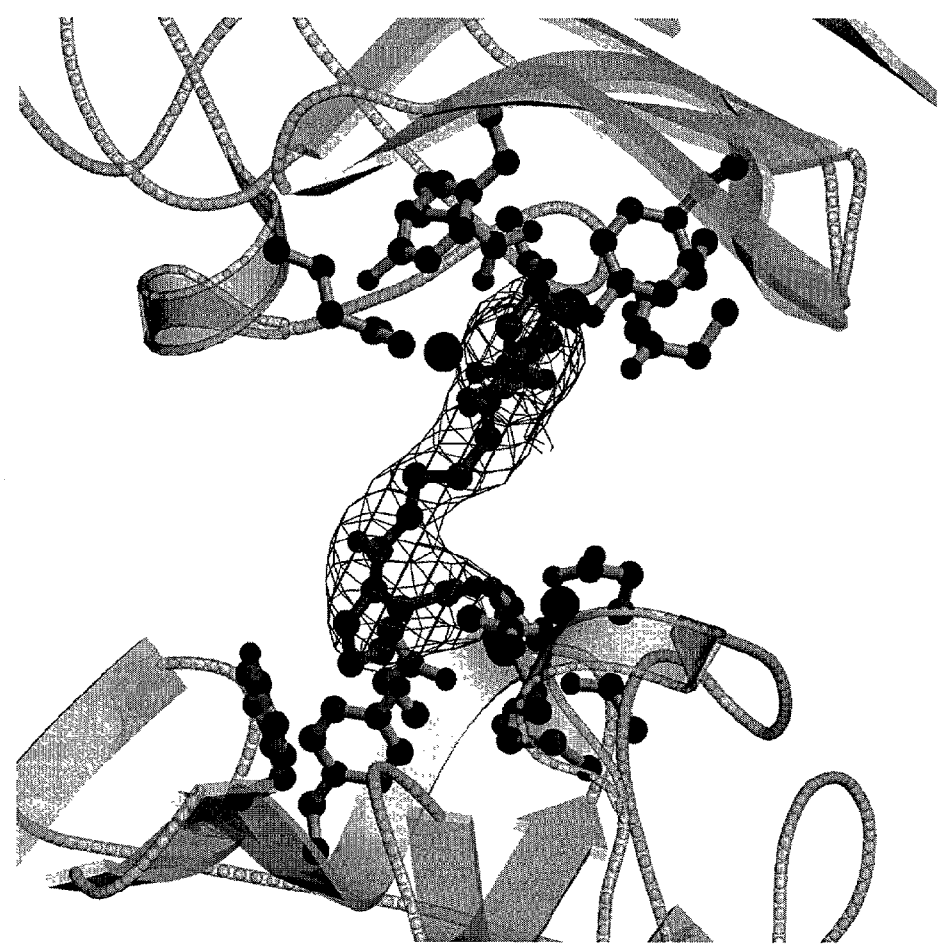
FIG. 2A shows a detailed view from FIG. 1
Figure 2B:
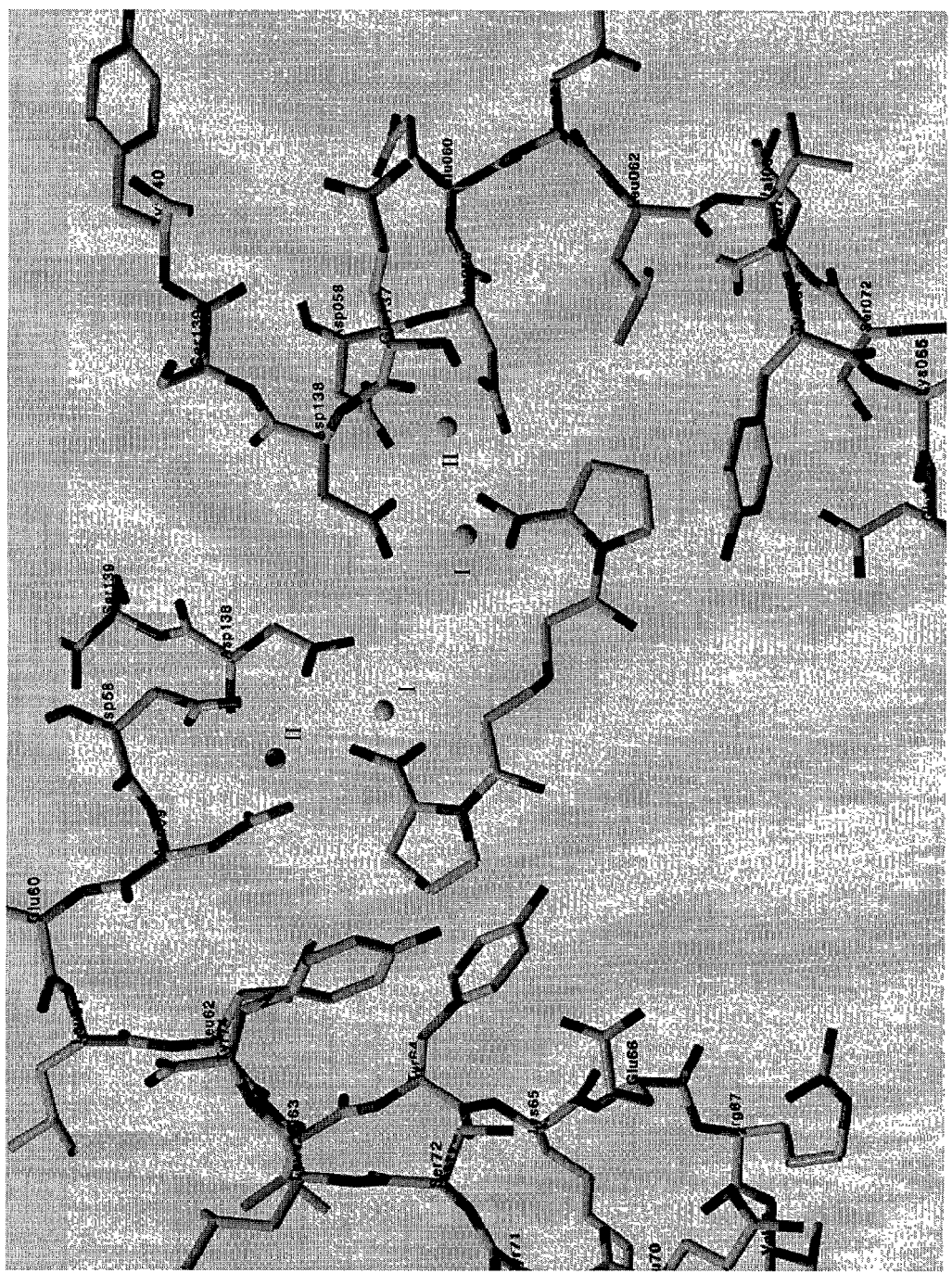
FIG. 2B shows a detailed alternative representation of part of FIG. 1.

The molecular model of two native pentameric SAP molecules cross linked by binding between them of the palindromic (R)-1-[6-(R)-2-Carboxy-pyrrolidin-1-yl]-6-oxo-hexanoyl]pyrrolidine-2-carboxylic acid molecule, is confirmed by the three dimensional X-ray crystal structure of the complex of SAP with the drug in the presence of calcium, as shown in representative views below (FIGS. 1 & 2). These findings are consistent with the published observations on the SAP-dAMP complex (10) and the chromatographic analysis (Table 1). FIG. 1 shows a three dimensional X-ray crystal structure of SAP complexed with (R)-1-[6-(R)-2-Carboxy-pyrrolidin-1-yl]-6-oxo-hexanoyl]pyrrolidine-2-carboxylic acid. In this Figure there is a side view showing two pentameric disc-like SAP molecules (9,10) edge on, cross linked by five (R)-1-[6-(R)-2-Carboxy-pyrrolidin-1-yl]-6-oxo-hexanoyl]pyrrolidine-2-carboxylic acid molecules, the terminal D-proline residues of each lying in the calcium-dependent ligand binding pocket of the apposed protomers. FIG. 2 shows a three dimensional X-ray crystal structure of SAP complexed with (R)-1-[6-(R)-2-Carboxy-pyrrolidin-1-yl]-6-oxo-hexanoyl]pyrrolidine-2-carboxylic acid. Detailed views are set out in FIGS. 2A and 2B showing two different representations of the ligand binding residues in the calcium-dependent ligand binding pockets of two apposed protomers of different SAP molecules, and the electron density and/or the molecular structure of (R)-1-[6-(R)-2-Carboxy-pyrrolidin-1-yl]-6-oxo-hexanoyl]pyrrolidine-2-carboxylic acid lying between them.

Experimental Studies of (R)-1-[6-(R)-2-Carboxy-pyrrolidin-1-yl]-6-oxo-hexanoyl]pyrrolidine-2-carboxylic acid in vivo In vivo studies of 1-(3-Mercapto-2-methyl-1-oxopropyl)-D-proline, the original lead compound, show that it both inhibits binding of SAP to experimentally induced amyloid deposits in mice and dissociates SAP that is already bound in the deposits. Studies with (R)-1-[6-(R)-2-Carboxy-pyrrolidin-1-yl]-6-oxo-hexanoyl]pyrrolidine-2-carboxylic acid confirmed that it is more active in these respects than 1-(3-Mercapto-2-methyl-1-oxopropyl-1-D-proline. The potency of (R)-1-[6-(R)-2-Carboxy-pyrrolidin-1-yl]-6-oxo-hexanoyl]pyrrolidine-2-carboxylic acid in vivo was initially considered to be consistent with its lower $IC_{50}$ value in vitro. However the decameric assembly of pentameric SAP molecules, induced by the cross linking capacity of the palindromic drug, is an abnormal molecular configuration which, according to the present invention, will be recognised in vivo and promptly cleared from the circulation. This action of the drug, leading to massive depletion of SAP from the plasma, makes a critical contribution to removal of SAP from the amyloid deposits because the SAP in amyloid is derived from, and in equilibrium with, the plasma SAP pool.

Figure 3:
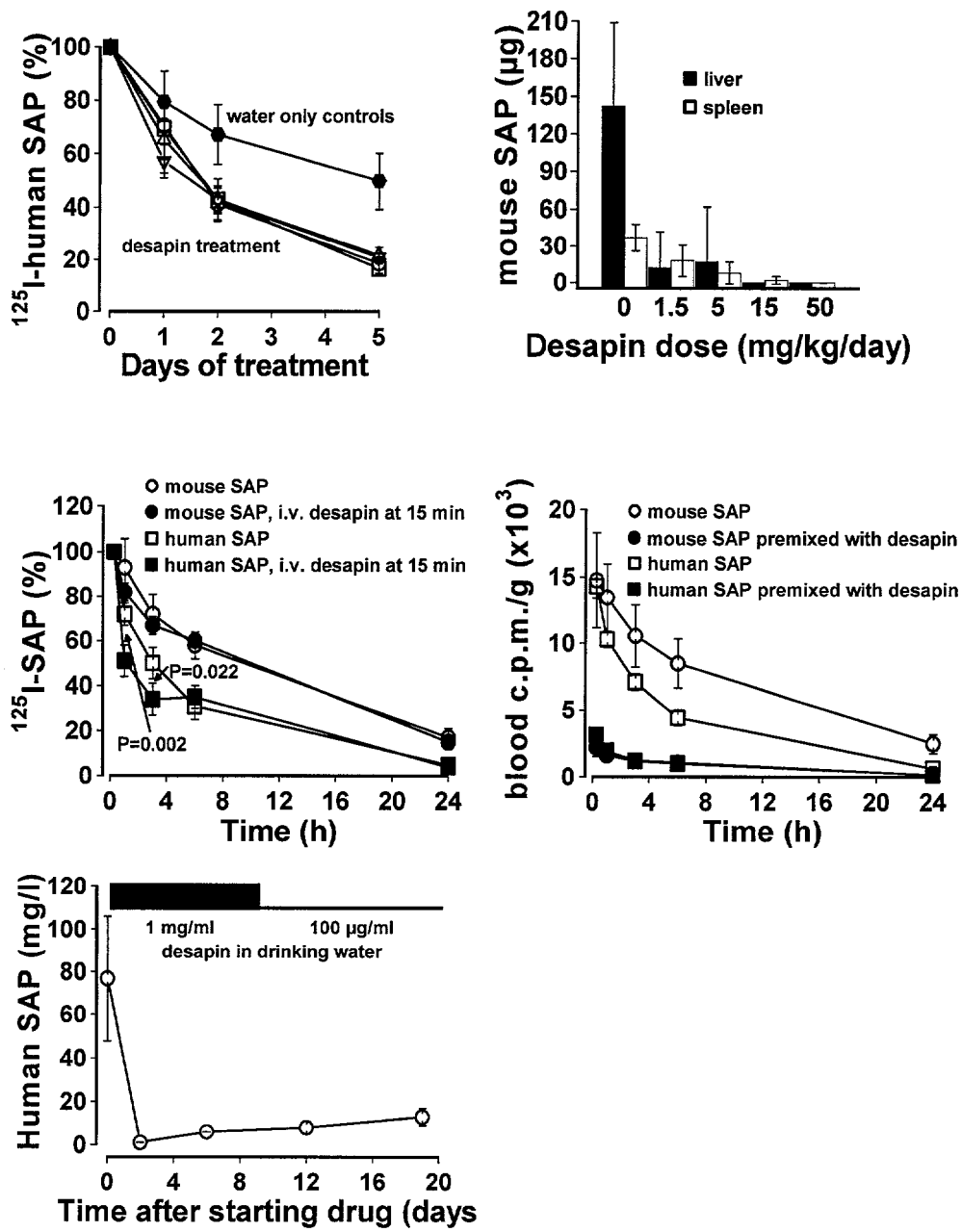
FIG. 3 shows the effect of an agent of the present invention on SAP in mice in vivo.

FIG. 3 shows as follows the effects of (R)-1-[6-(R)-2-Carboxy-pyrrolidin-1-yl]-6-oxo-hexanoyl] pyrrolidine-2-carboxylic acid on SAP in mice in vivo. Upper panel: groups of 10 age, sex and weight matched mice with experimentally induced reactive systemic AA amyloidosis were given a single loading dose of $^{125}$I-labelled human SAP on day −1, and received implanted osmotic minipumps delivering the doses shown of (R)-1-[6-(R)-2-Carboxy-pyrrolidin-1-yl]-6-oxo-hexanoyl]pyrrolidine-2-carboxylic acid (designated on the figures as "desapin" for convenience). Clearance from the amyloid deposits, catabolism and excretion of the human SAP tracer were monitored globally by whole body counting of the mice (left), and the total amount of mouse SAP in the amyloidotic organs was determined after killing the animals on day 5 (right). Middle panel, left: 4 groups each of 10 age, sex and weight matched mice with experimentally induced reactive systemic AA amyloidosis received an intravenous injection of $^{125}$I-labelled pure human or mouse SAP at time zero and were then bled after 15 minutes and at the other times shown. Immediately after the 15 minute bleed, two groups, one that had received human SAP and the other mouse SAP, received a single intraperitoneal injection of 5 mg of (R)-1-[6-(R)-2-Carboxy-pyrrolidin-1-yl]-6-oxo-hexanoyl]pyrrolidine-2-carboxylic acid (desapin). Tracer remaining in the circulation is expressed as the mean (SD) percentage of the amount at the 15 minute time point for each group. Middle panel, right: groups each of 10 age, sex and weight matched mice with experimentally induced reactive systemic AA amyloidosis received an intravenous injection of $^{125}$I-labelled pure human or mouse SAP at time zero and were then bled after 15 minutes and at the other times shown. In one of each of the pairs of groups receiving mouse or human SAP respectively, the tracer had been mixed with (R)-1-[6-(R)-2-Carboxy-pyrrolidin-1-yl]-6-oxo-hexanoyl]pyrrolidine-2-carboxylic acid (desapin) and incubated in vitro before injection into the animals. Tracer remaining in the circulation is expressed as mean (SD) total radioactivity per gram of blood in each group. Bottom panel: effect of administration of (R)-1-[6-(R)-2-Carboxy-pyrrolidin-1-yl]-6-oxo-hexanoyl]pyrrolidine-2-carboxylic acid (desapin) in the drinking water at the concentrations shown, on circulating human SAP values in human SAP transgenic mice. Mice of approximately 20 g body weight consume about 3 ml water per day.

(R)-1-[6-(R)-2-Carboxy-pyrrolidin-1-yl]-6-oxo-hexanoyl]pyrrolidine-2-carboxylic acid was not metabolised in mice and was very rapidly excreted, predominantly in the urine, with a small amount in the bile. However, even intermittent intraperitoneal or subcutaneous injection of (R)-1-[6-(R)-2-Carboxy-pyrrolidin-1-yl]-6-oxo-hexanoyl] pyrrolidine-2-carboxylic acid inhibited uptake of radiolabelled human SAP tracer into experimentally induced mouse AA amyloid deposits. When (R)-1-[6-(R)-2-Carboxy-pyrrolidin-1-yl]-6-oxo-hexanoyl]pyrrolidine-2-carboxylic acid was administered by continuous infusion for 5 days via an indwelling osmotic pump, it dissociated both radiolabelled human SAP tracer, with which the amyloid deposits had previously been loaded, and all the endogenous mouse SAP in the deposits (FIG. 3). Even 50 μg/kg/day of (R)-1-[6-(R)-2-Carboxy-pyrrolidin-1-yl]-6-oxo-hexanoyl]pyrrolidine-2-carboxylic acid significantly dissociated human SAP from the deposits (not shown), but 1.5 mg/kg/day was required to dissociate any endogenous mouse SAP significantly, and there was a clear dose response effect up to 15 mg/kg/day, which removed all the mouse SAP (FIG. 3). A single intraperitoneal injection of 5 mg of (R)-1-[6-(R)-2-Carboxy-pyrrolidin-1-yl]-6-oxo-hexanoyl]pyrrolidine- 2-carboxylic acid accelerated the plasma clearance of radiolabelled human SAP tracer in normal mice, but had no significant effect on the clearance of radiolabelled mouse SAP (FIG. 3). However, when either radiolabelled mouse or human SAP was preincubated with (R)-1-[6-(R)-2-Carboxy-pyrrolidin-1-yl]-6-oxo-hexanoyl]pyrrolidine-2-carboxylic acid in vitro, before intravenous injection into normal mice, both tracers were extremely rapidly cleared (FIG. 3). The SAP-(R)-1-[6-(R)-2-Carboxy-pyrrolidin-1-yl]-6-oxo-hexanoyl]pyrrolidine-2-carboxylic acid complex is evidently recognised as abnormal in vivo and swiftly removed from the circulation, but is apparently formed and/or cleared less efficiently in vivo with mouse SAP compared to human SAP. Remarkably, despite very limited oral bioavailability, administration of (R)-]-[6-(R)-2-Carboxy-pyrrolidin-1-yl]-6-oxo-hexanoyl]pyrrolidine-2-carboxylic acid in the drinking water to human SAP transgenic mice, which have mean plasma values of about 80 mg/l of human SAP, rapidly depleted their circulating human SAP (FIG. 3). The human SAP transgenic animals do not have any circulating mouse SAP, but neither oral administration, nor intermittent injection or continuous infusion, of (R)-1-[6-(R)-2-Carboxy-pyrrolidin-1-yl]-6-oxo-hexanoyl]pyrrolidine-2-carboxylic acid to normal wild type mice, caused depletion of their circulating SAP.

Figure 4:
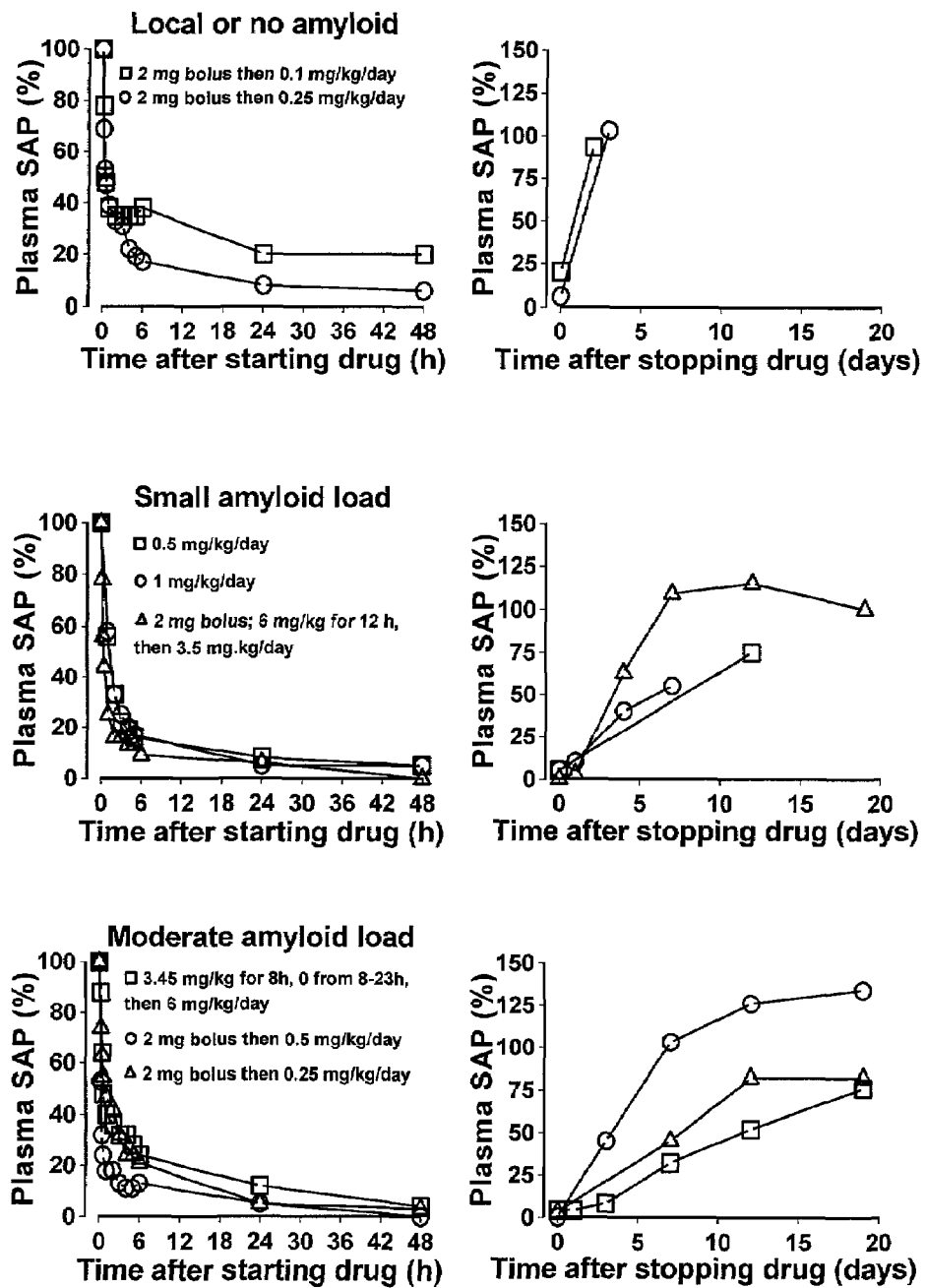
FIG. 4 shows the effect of infusion of an agent of the invention on plasma SAP values in patients with systemic amyloidosis.
Figure 4:
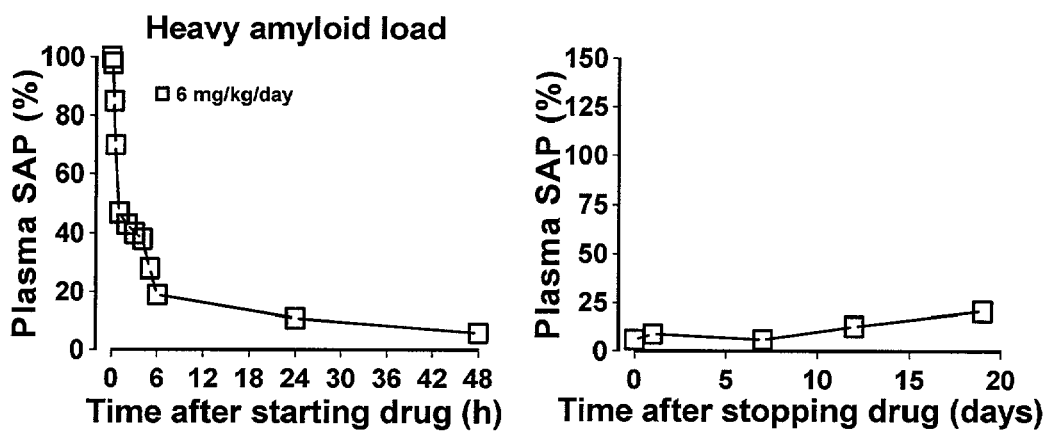

Clinical Studies of (R)-1-[6-(R)-2-Carboxy-pyrrolidin-1-yl]-6-oxo-hexanoyl]pyrrolidine-2-carboxylic acid in human amyloidosis FIG. 4 shows the effect of intravenous infusion of (R)-1-[6-(R)-2-Carboxy-pyrrolidin-1-yl]-6-oxo-hexanoyl]pyrrolidine-2-carboxylic acid on plasma SAP values in patients with systemic amyloidosis. Patients with different forms of systemic amyloidosis, and with varying amyloid loads received the doses of the drug shown for a period of 48 h. Circulating SAP values were measured by electroimmunoassay (24) in samples taken during and after the infusion, at the times shown. Each line represents a different individual patient.

(R)-1-[6-(R)-2-Carboxy-pyrrolidin-1-yl]-6-oxo-hexanoyl]pyrrolidine-2-carboxylic acid was administered for 48 h by intravenous infusion to 8 patients with systemic amyloidosis (7 with AL and one with AA type), one patient with minor localised AL amyloidosis, and one who is a carrier of the amyloidogenic Ala60 transthyretin variant but has no clinical amyloidosis. There was dramatic, rapid, and consistent depletion of circulating SAP in all subjects. In initial studies with slow continuous infusion, the SAP concentration started to fall when about 2 mg of (R)-1-[6-(R)-2-Carboxy-pyrrolidin-1-yl]-6-oxo-hexanoyl]pyrrolidine-2-carboxylic acid had been given, and in subsequent studies this amount was therefore injected as a bolus at the outset, followed by infusion at the rates shown (FIG. 4). At an infusion rate of 0.1 mg/kg/day, SAP depletion was slower and less complete, but at 0.25 mg/kg/day and all higher rates up to a maximum of 6 mg/kg/day, SAP was almost completely cleared from the plasma by the end of the infusion, regardless of the amyloid load (FIG. 4). However, after drug infusion had ceased, the plasma SAP concentration rapidly returned to normal in the individuals with little or no amyloid, whereas this recovery was markedly delayed in subjects with significant amyloidosis. In the one patient with a very heavy amyloid load, the plasma SAP concentration remained below 25% of its initial value 20 days after the infusion. Most of the daily production of SAP, which is about 50–100 mg per day (15), was evidently distributing into the amyloid deposits before becoming available to replete the plasma pool. This is very strong indirect evidence that even such a brief infusion of (R)-1-[6-(R)-2-Carboxy-pyrrolidin-1-yl]-6-oxo-hexanoyl]pyrrolidine-2-carboxylic acid had substantially depleted the amyloid-associated SAP.

Figure 5:
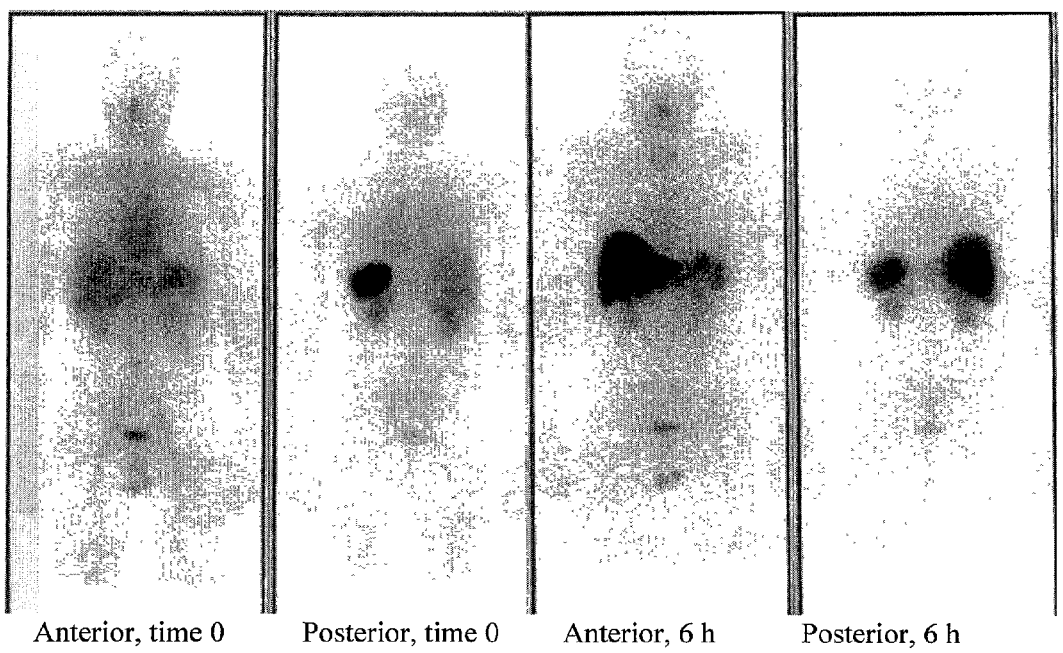
FIG. 5 shows the effect of the agent over six hours using $^{123}$I-SAP scintigraphy.

FIG. 5 shows whole body $^{123}$I-SAP scintigraphy before and 6 h after starting infusion of (R)-1-[6-(R)-2-Carboxy-pyrrolidin-1-yl]-6-oxo-hexanoyl]pyrrolidine-2-carboxylic acid. This patient, with a modest load of AL amyloid in the spleen and kidneys, had notable blood pool background of tracer in the heart and circulation before administration of the drug. At 6 h the blood pool background is completely absent and the liver, which is the only site of catabolism of SAP in vivo (16,17), has taken up the tracer whilst the intensity of SAP signal from the amyloidotic spleen and kidneys is significantly reduced (organ counts not shown).

Figure 6:
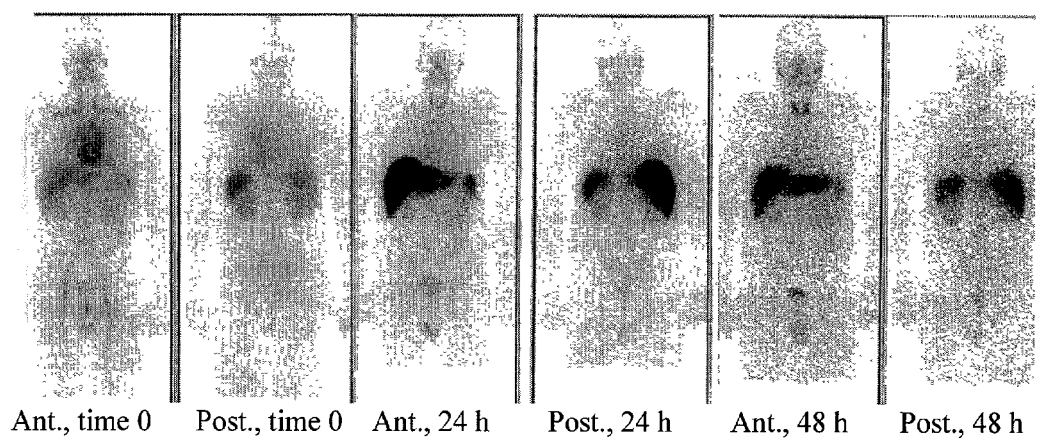
FIG. 6 shows the effect of the agent up to 48 hours using $^{123}$I-SAP scintigraphy.

FIG. 6 shows whole body $^{123}$I-SAP scintigraphy before and 24 h and 48 h after starting infusion of (R)-1-[6-(R)-2-Carboxy-pyrrolidin-1-yl]-6-oxo-hexanoyl]pyrrolidine-2-carboxylic acid in a second patient. This patient, with modest load of AL amyloid in the spleen and kidneys, had notable blood pool background of tracer in the heart and circulation before administration of the drug. At 24 h and 48 h the blood pool background is completely absent and the liver, which is the only site of catabolism of SAP in vivo (16,17), has taken up the tracer and catabolic products are being excreted in the urine, as shown by the bladder signal. The intensity of SAP signal from the amyloidotic spleen and kidneys is significantly reduced: at 24 h spleen counts are 85% of time 0, kidneys 77%; at 48 h, spleen 54%, kidneys 50%.

Direct evidence for depletion of SAP from amyloid in the organs and for the mechanism of action of (R)-1-[6-(R)-2-Carboxy-pyrrolidin-1-yl]-6-oxo-hexanoyl]pyrrolidine-2-carboxylic acid was obtained by quantitative whole body scintigraphy using $^{123}$I-SAP as a tracer. Each patient received a standard dose of $^{123}$I-SAP 24 h before the (R)-1-[6-(R)-2-Carboxy-pyrrolidin-1-yl]-6-oxo-hexanoyl] pyrrolidine-2-carboxylic acid infusion started and was scanned immediately before treatment to provide a baseline image and values for localisation of tracer to the amyloid deposits. They were then scanned at intervals thereafter, up to the end of the 48 h infusion. (R)-1-[6-(R)-2-Carboxy-pyrrolidin-1-yl]-6-oxo-hexanoyl]pyrrolidine-2-carboxylic acid caused dramatic clearance of tracer from the plasma, exactly paralleling both in the scintigraphic images and in counting of blood samples, the SAP depletion monitored by immunoassay of the serum. By 6 h after starting treatment, and persisting thereafter, the blood pool signal virtually disappeared (FIGS. 5, 6), and there was striking accumulation of tracer in the liver, identifying this organ as the site to which (R)-1-[6-(R)-2-Carboxy-pyrrolidin-1-yl]-6-oxo-hexanoyl]pyrrolidine-2-carboxylic acid caused clearance of the circulating SAP. At the same time there was a marked decrease in the retention of tracer in amyloid deposits elsewhere, exemplified by the spleen and kidneys, in contrast to the usual situation in control untreated amyloidosis patients (Table 2; FIG. 6).

TABLE 2

(R)-1-[6-(R)-2-Carboxy-pyrrolidin-1-yl]-6-oxo-hexanoyl]pyrrolidine-2-carboxylic acid rapidly clears circulating SAP to the liver and depletes SAP from visceral amyloid deposits

| | $^{123}$I-SAP retention [mean (SD) %] | | | | |
|---|---|---|---|---|---|
| | Liver Time after tracer injection | | | Spleen Time after tracer injection | |
| Treatment | 24 h | 48 h | No. of patients | 24 h | 48 h | No. of patients |
| None | 100 | 78 (8) | 12 | 100 | 86 (25) | 14 |
| Drug | 100 | 125 (20) P < 0.0001 | 7 | 100 | 54 (18) P = 0.008 | 7 |

All patients had systemic AL amyloidosis and received a standard intravenous tracer dose of $^{123}$I-SAP at time zero. After whole body quantitative scintigraphic imaging at 24 h, uptake in liver and spleen were taken as 100% for each individual. Intravenous infusion of the drug (R)-1-[6-(R)-2-Carboxy-pyrrolidin-1-yl-6-oxo-hexanoyl]pyrrolidine-2-carboxylic acid was then started and scintigraphy with organ counting was repeated at 48 h. The controls received no treatment. Significance of differences between the two groups was sought by t-test.

It has previously been demonstrated in mice that the liver, and specifically the hepatocyte, is the only significant site of clearance and catabolism of both mouse and human SAP in vivo (16). Furthermore, asialo-human SAP is instantly cleared by the liver in man, via the hepatocyte asialoglycoprotein receptor, and this process has been imaged using $^{123}$I-asialo SAP (17). (R)-1-[6-(R)-2-Carboxy-pyrrolidin-1-yl]-6-oxo-hexanoyl]pyrrolidine-2-carboxylic acid evidently triggers similarly rapid hepatic uptake of SAP in vivo, leading to virtually total depletion of circulating SAP. This promotes redistribution of SAP from the tissues to the plasma and supplements the effect of (R)-1-[6-(R)-2-Carboxy-pyrrolidin-1-yl]-6-oxo-hexanoyl]pyrrolidine-2-carboxylic acid as a competitive inhibitor of SAP binding to amyloid fibrils, thereby leading to highly efficient removal of SAP from amyloid deposits.

Figure 7:
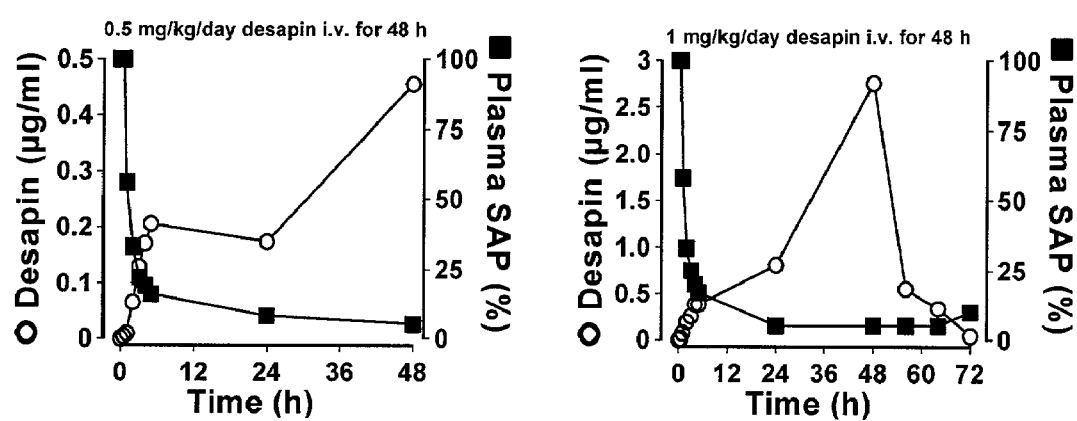
FIG. 7 shows the plasma concentration of the agent and its effect on SAP during intravenous infusion.

FIG. 7 shows plasma concentration of (R)-1-[6-(R)-2-Carboxy-pyrrolidin-1-yl]-6-oxo-hexanoyl]pyrrolidine-2-carboxylic acid and of SAP during 48 h infusion. Two individual patients with systemic amyloidosis and moderate amyloid loads received (R)-1-[6-(R)-2-Carboxy-pyrrolidin-1-yl]-6-oxo-hexanoyl]pyrrolidine-2-carboxylic acid (desapin) by intravenous infusion at the steady rates shown. Circulating SAP concentrations started to fall almost immediately and had halved when the concentrations of drug and SAP protomer were equimolar.

The potency of (R)-]-[6-(R)-2-Carboxy-pyrrolidin-1-yl]-6-oxo-hexanoyl]pyrrolidine-2-carboxylic acid in depleting circulating SAP was remarkable, with SAP values falling when the concentration ratio of drug to SAP pentamer in the plasma approached equimolar (FIG. 7). In vitro gel filtration studies showed that even this very low concentration of drug is sufficient to generate some SAP dimers (Table 3), that is pairs of pentameric SAP molecules cross linked by (R)-1-[6-(R)-2-Carboxy-pyrrolidin-1-yl]-6-oxo-hexanoyl]pyrrolidine-2-carboxylic acid molecules to form the decameric assembly seen in the crystal structure (FIGS. 1, 2). This is evidently the species recognised as abnormal and promptly cleared by the liver.

TABLE 3

Molecular assembly of SAP in whole human serum in the presence of (R)-1-[6-(R)-2-Carboxy-pyrrolidin-1-y]-6-oxo-hexanoyl]pyrrolidine-2-carboxylic acid in vitro

| Drug:protein molar ratio | Calcium present | Protein | Elution volume (ml) | Molecular assembly |
|---|---|---|---|---|
| No drug | − | CRP | 12.0–12.5 | Pentamer |
| No drug | + | CRP | 12.0–12.5 | Pentamer |
| 1:1 | + | CRP | 12.0–12.5 | Pentamer |
| 10:1 | + | CRP | 12.0–12.5 | Pentamer |
| 100:1 | + | CRP | 12.0–12.5 | Pentamer |
| No drug | − | SAP | 10.5–11.5 | Decamer |
| No drug | + | SAP | 7.0–8.0 | High MW aggregates |
| 1:1 | + | SAP | 7.0–8.0 & 10.0–10.5 | High MW aggregates Decamer |
| 10:1 | + | SAP | 7.0–8.0 & 10.0–10.5 | High MW aggregates Decamer |
| 100:1 | + | SAP | 10.0–10.5 | Decamer |

Aliquots of a single pool of whole normal human serum, containing SAP and CRP were mixed with (R)— 1-[6-(R)-2-Carboxy-pyrrolidin-1-yl]-6-oxo-hexanoyl]pyrrolidine-2-carboxylic acid at the molar ratios shown, with respect to pentraxin protomer, and analysed by size exclusion chromatography precisely as described previously (14). The mixtures and the column eluants contained either no calcium ions or 2 mM calcium, and the concentrations of drug appropriate to maintain the molar ratios indicated above. SAP in whole serum is a stable soluble pentameric assembly of protomers, stabilised by the presence of the normal high concentration of serum albumin. However as SAP is separated from serum albumin during gel filtration with a calcium containing eluant, the SAP autoaggregates and elutes entirely as high molecular weight polymers in the void volume of the column. This is because, in the absence of a specific ligand to which it can bind, isolated human SAP is insoluble in the presence of calcium (14). However in the absence of calcium, where no ligand binding or autoaggregation can occur, SAP forms stable decamers, providing an excellent marker for the elution volume of this molecular assembly (14). Human CRP is a stable pentamer either in the presence or absence of calcium and thus provides a robust marker for the elution position of that molecular form (14).

Even at an equimolar concentration of the drug, some of the SAP was solubilised as stable drug-decamer complexes, and at 100 fold molar excess of drug, all the SAP was in this form.

The potency of (R)-1-[6-(R)-2-Carboxy-pyrrolidin-1-yl]-6-oxo-hexanoyl]pyrrolidine-2-carboxylic acid was confirmed by the observation that subcutaneous injection of just 0.25 mg/kg/day, given in 12 hourly divided doses, had the same effect on plasma SAP (FIG. 8) as intravenous infusion of the drug.

Figure 8:
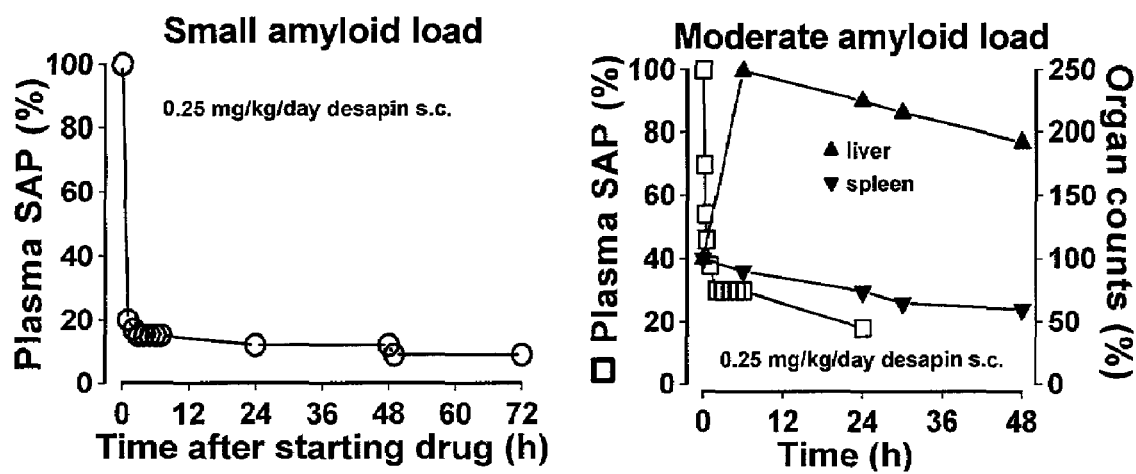
FIG. 8 shows the effect of subcutaneous injection of the agent in patients with systemic amyloidosis.

FIG. 8 shows the effect of (R)-1-[6-(R)-2-Carboxy-pyrrolidin-1-yl]-6-oxo-hexanoyl]pyrrolidine-2-carboxylic acid administration by subcutaneous injection on circulating SAP vales and visceral organ retention of $^{123}$I-SAP tracer. The doses of (R)-1-(R)-2-Carboxy-pyrrolidin-1-yl]-6-oxo-hexanoyl]pyrrolidine-2-carboxylic acid (desapin) shown were given by 12 hourly subcutaneous injections to two individual patients with systemic amyloidosis, and with small and moderate amyloid loads respectively. The disappearance of circulating SAP was effectively the same as during intravenous infusion of the drug, and in the patient illustrated in the right panel, who had received a tracer dose of $^{123}$I-SAP, there was accumulation of SAP in the liver and accelerated clearance from the spleen.

Conclusion (R)-1-[6-(R)-2-Carboxy-pyrrolidin-1-yl]-6-oxo-hexanoyl]pyrrolidine-2-carboxylic acid specifically targets SAP in vivo, through the specific ligand binding capacity of SAP, but additionally, as a consequence of the drug's palindromic structure, according to the present invention, it causes aggregation of native pentameric SAP molecules into decameric drug SAP complexes that are then promptly cleared by the liver. This novel effect was not intended during development of (R)-1-[6-(R)-2-Carboxy-pyrrolidin-1-yl]-6-oxo-hexanoyl]pyrrolidine-2-carboxylic acid as an inhibitor of SAP binding to amyloid fibrils, and was neither sought nor expected. It represents a well documented example of the present invention and it dramatically enhances the dissociation of SAP from amyloid deposits, which is the therapeutic objective in amyloidosis. Such targeted pharmacological depletion of a circulating plasma protein represents a novel, previously undescribed mechanism of drug action, with broad applicability to many different proteins and disease processes.

Transthyretin

Transthyretin (TTR), formerly known as prealbumin, is a normal plasma protein produced in the liver and also by the choroid plexus in the brain. It transports both thyroid hormone (thyroxine and tri-iodothyronine) and retinol binding protein (RBP) in the plasma. Although these are presumably important physiological functions, mice with targeted deletion of the TTR gene and complete absence of TTR grow and develop normally, are fertile and have no abnormal phenotype. This is probably because retinol (vitamin A) can be supplied adequately without the need for carriage of RBP by TTR, and because there is another plasma protein that specifically binds thyroid hormone, thyroxine binding globulin (TBG). Indeed TBG binds thyroxine with much greater affinity than TTR and is evidently more important in regulating hormonal availability and function.

Normal wild type TTR is inherently amyloidogenic and at post mortem examination almost all individuals over the age of 80 years have microscopic deposits of TTR amyloid in the heart, blood vessel walls, choroid plexus or elsewhere. In some subjects the deposits are much more substantial and may cause clinical problems, a condition known as senile systemic amyloidosis. Importantly, there are over 60 mutations in the human TTR gene, encoding single amino acid substitutions in variant TTR proteins, that cause the very serious and generally fatal form of autosomal dominant hereditary systemic amyloidosis known as familial amyloid polyneuropathy. This condition is variably penetrant but when expressed it is invariably fatal with onset in early to middle adult life and inexorable progression of various combinations of peripheral and autonomic neuropathy, cardiac, renal, vascular and ocular involvement, leading to death within 5–15 years. There are thousands of affected kindreds throughout the world. The only effective treatment is liver transplantation, which replaces the source of the amyloidogenic variant plasma TTR with a source of normal wild type TTR, and over 1000 such operations have been performed world wide since the procedure was introduced in 1991 (18,19). Once the pathogenic variant TTR is replaced, deposition of amyloid is halted and the existing deposits regress with clinical benefit, provided the patient's condition is not already too advanced. However liver transplantation is clearly a major and dangerous procedure, especially in these patients with multiple organ system damage by amyloid, and there is an insoluble shortage of donor organs. Furthermore, satisfactory outcomes have largely been confined to patients with the most common amyloidogenic TTR variant, Met30Val. It has lately become apparent that in patients with other amyloidogenic mutations of the TTR gene, liver transplantation does not halt progression of amyloid deposition, especially in the heart, and despite the presence only of wild type TTR in the plasma the outcome remains poor. There is thus a pressing need for new therapeutic approaches.

One such approach is the use of drugs that are bound with high affinity by TTR, in order to stabilise the native fold of the TTR molecule and prevent the unfolding and subsequent refolding into the pathogenic amyloid cross-β structure that underlies amyloid fibrillogenesis. Low molecular weight molecules suitable for use as drugs of this type have been developed and effectively inhibit formation of amyloid fibrils by isolated TTR in vitro (20). Furthermore some of these compounds have been shown to be specifically bound with high affinity, not just by isolated TTR, but also by TTR within the environment of whole plasma (21). This is critically important because drugs in general are often bound by multiple plasma proteins, especially albumin which comprises 57% by weight of all plasma proteins. Also, in particular, drugs bound by TTR in the binding pocket that specifically recognises thyroid hormone, may be bound by TBG as well.

According to the present invention, palindromic drugs that are bound by TTR in vivo, and can then cross link TTR molecules, aggregating them and thereby marking them for prompt clearance from the circulation, are suitable for use in depleting TTR and therefore treating and preventing TTR amyloidosis. The ligand head groups of such drugs may be compounds 9–11 in Purkey et al (21), as set out below. The linker joining them may be a series of methylene groups as used in the SAP depleting compound, (R)-1-[6-(R)-2-Carboxy-pyrrolidin-1-yl]-6-oxo-hexanoyl]pyrrolidine-2-carboxylic acid, detailed above, or another aliphatic and/or aromatic chain of suitable length and other properties.

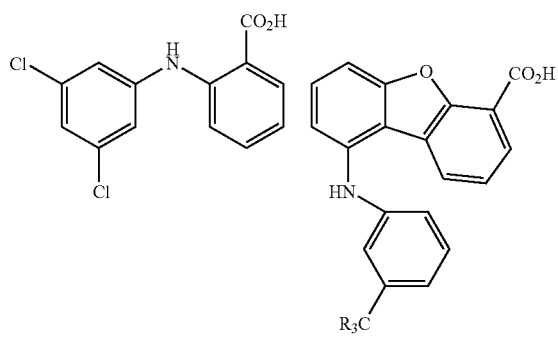

or

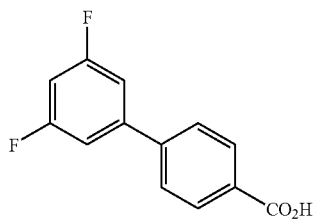

When these ligands are bound by TTR, the ring bearing the carboxylate sits deeply in the cavity within the TTR tetramer, and the ring bearing the halogen atoms is peripheral and exposed on the surface of the ligand-TTR complex. The attachment point for the correct bond or linker is preferably a point on the aromatic ring bearing the halogen or halogen-containing substituents. A more preferred attachment point for the linker, forming compounds according to the present invention, is the ring carbon lying between the two ring carbons that have halogens attached, or a carbon of the ring distal to the carboxylate bearing ring in the middle example above.

Lysozyme

Lysozyme is a glycanase enzyme (EC 3.2.1.17) widely distributed in animals, plants and lower organisms. It specifically cleaves the glycosidic bond between the C-1 of N-acetylmuramic acid and the C-4 of N-acetylglucosamine in bacterial peptidoglycan, and is thus a 1,4-β-N-acetylmuramidase. In man lysozyme is secreted in saliva, tears and other external secretions, is the major secreted product of macrophages and is also produced by hepatocytes and the Paneth cells of the intestine. The functions of lysozyme in man are not well understood, although by virtue of its capacity to digest the cell walls of susceptible bacteria it may contribute to host defence. It is also highly cationic and becomes tightly associated with anionic glycosaminglycans and is concentrated in cartilage. The first mutations to be discovered in the human lysozyme gene are associated with a form of hereditary systemic amyloidosis for which there is no effective treatment (22). The variant lysozyme molecules are amyloidogenic because the single residue substitutions they contain render them less stable than wild type lysozyme (23). They spontaneously unfold under physiological conditions, populating partly unfolded states that have a high propensity to refold and aggregate in the abnormal, pathogenic, amyloid cross-β fibrillar configuration (23).

According to the present invention, palindromic drugs that are bound by lysozyme in vivo, and can then cross link lysozyme molecules, aggregating them and thereby marking them for prompt clearance from the circulation, are suitable for use in depleting lysozyme and therefore treating and preventing lysozyme amyloidosis. The ligand head groups of such drugs are stereochemically related to lysozyme substrates but are bound and not cleaved by the enzyme. For example, a disaccharide or oligosaccharide analogue containing at least N-acetyl muramic acid linked via its C 1 atom to the C4 atom of N-acetyl glucosamine, with the O atom of the 1,4 β glycosidic linkage replaced by a carbon or other non-O atom, is bound by lysozyme but cannot be hydrolysed. Appropriate substituents, such as fluorine or nitrogen, on the critical C atom, that replaces the hydrolysable O atom of the glycosidic linkage, can enable important hydrogen bonding contributed by the replaced O atom to be retained. The linker joining the ligands may be a series of methylene groups as used in (R)-1-[6-(R)-2-Carboxy-pyrrolidin-1-yl]-6-oxo-hexanoyl]pyrrolidine-2-carboxylic acid, or another aliphatic and/or aromatic chain of suitable length and other properties. The preferred attachment points for the linker are positions 2 (N-acetyl) or 6 (OH) on any of the pyranose rings, as these positions point to the exterior in the oligosaccharide-lysozyme complex.

$β_2$-Microglobulin $β_2$-microglobulin is a single chain protein of Mr 11,815 that is non-covalently associated with all class I MHC molecules on the surface of cells. It is produced at the rate of about 200 mg per day in man and is cleared and catabolised exclusively in the kidney. Plasma levels of β2-microglobulin therefore rise in renal failure and neither haemodialysis nor peritoneal dialysis are effective in clearing $β_2$-microglobulin. In patients with end stage renal failure on dialysis, the plasma concentration of $β_2$-microglobulin reaches 50–70 mg/l, compared to the normal of about 2 mg/l, and after about 5–7 years of dialysis most such individuals suffer from deposition of $β_2$-Microglobulin amyloid, especially around bones and joints. This leads to serious morbidity and mortality among the approximately 1 million patients who are on long term dialysis world wide. The only effective treatment is renal transplantation, which provides the only possible route for efficient removal of $β_2$-microglobulin, but transplantation is available only for a small minority of end stage renal failure patients.

According to the present invention, palindromic drugs that are bound by $β_2$-microglobulin in vivo, and can then cross link $β_2$-microglobulin molecules, aggregating them and thereby marking them for prompt clearance from the circulation, are suitable for use in depleting $β_2$-microglobulin and therefore treating and preventing $β_2$-microglobulin amyloidosis. Specific ligands for $β_2$-microglobulin, bound with reasonable affinity, can be identified by high throughput screening of chemical libraries. $β_2$-microglobulin shares substantial sequence homology and its tertiary fold with immunoglobulin light chains, and its crystal structure is known at atomic resolution, enabling and greatly facilitating rational molecular design.

Amyloid Fibril Precursor Proteins in General

It is well established that in all forms of amyloidosis in which it is possible to eliminate the supply of amyloid fibril precursor proteins, deposition of new amyloid ceases and existing deposits either stabilise or regress leading to clinical benefit. This has been detailed in the examples above but it applies to all types of amyloidosis, including those associated with Alzheimer's disease, the transmissible spongiform encephalopathies including bovine spongiform encephalopathy and variant Creutzfeldt-Jakob disease, and type 2, maturity onset diabetes mellitus.

Drugs according the present invention, specific for each particular amyloid fibril precursor protein, are applicable to all these and other amyloid related diseases. Furthermore, heterobifunctional drugs according to the present invention, in which one species of ligand head is bound specifically by SAP and the other by the target amyloidogenic protein, are especially advantageous. They promote efficient removal of the target protein itself, they do so with enhanced efficiency by engaging the powerful clearance mechanism that operates on aggregated SAP, and they also simultaneously eliminate SAP itself. Since SAP contributes to the pathogenesis of all types of amyloidosis, the simultaneous removal of both the amyloidogenic fibril proteins and the SAP has synergistic therapeutic benefit.

Autoantibodies

The acquired immune system of the body has the capacity to make highly specific, high affinity, antibodies against essentially any molecule. Molecules that induce antibody formation are called antigens, and the submolecular region that is actually recognised and bound by an antibody is called an epitope. Normally antibodies are formed predominantly in response to foreign antigens from outside the body and are of central importance in host defence against microbial and parasitic infection. Apart from low grade responses that contribute to clearance of damaged autologous constituents, and other responses that are involved in immune regulation, the immune system is tolerant towards the body's own molecules and does not produce autoantibodies against them. However in autoimmune diseases, tolerance is broken and aberrant autoantibodies are produced that bind to self constituents and lead to inflammation, cell death, and tissue damage. There are many different forms of autoimmune disease, depending on the precise specificity of the autoantibodies and whether they are directed against organ or tissue specific autoantigens, or are non-organ specific. However in most autoimmune diseases the specificity of the pathogenic autoantibodies and the identities of the autoantigens and many of their key epitopes are known.

According to the present invention, palindromic drugs that are bound specifically by particular pathogenic autoantibodies in vivo, and can then cross link them, producing aggregation leading to prompt clearance from the circulation, are suitable for use in depleting these autoantibodies and therefore treating autoimmune diseases.

Examples of pathogenic autoantibodies and the diseases they cause, that are suitable for treatment according to the present invention include: anti-DNA antibodies in systemic lupus erythematosus (SLE) and related collagen diseases, anti-immunoglobulin antibodies (rheumatoid factors) in rheumatoid arthritis and related idiopathic arthritides, anti-phospholipid antibodies in SLE and related collagen diseases, all the organ specific autoantibodies in all the organ specific autoimmune diseases including those that affect the endocrine organs, the liver, gut, skin, muscle, central and peripheral nervous systems, eyes, ears, heart, blood vessels, lungs and other viscera, and all the autoimmune diseases affecting the red cells, white cells and platelets of the blood and their precursors in the bone marrow. In these and all the other autoimmune diseases, the present invention provides for creation of palindromic drug molecules comprising the relevant specific epitope or epitopes as the ligand head groups, joined by a linker structure.

REFERENCES

1. Hind, C. R. K., Collins, P. M., Caspi, D., Baltz, M. L. and Pepys, M. B. (1984) Specific chemical dissociation of fibrillar and non-fibrillar components of amyloid deposits. *Lancet*, ii: 376–378.
2. Tennent, G. A., Lovat, L. B. and Pepys, M. B. (1995) Serum amyloid P component prevents proteolysis of the amyloid fibrils of Alzheimer's disease and systemic amyloidosis. *Proc. Natl. Acad. Sci. USA*, 92: 4299–4303.
3. Pepys, M. B., Tennent, G. A., Booth, D. R., Bellotti, V., Lovat, L. B., Tan, S. Y., Persey, M. R., Hutchinson, W. L., Booth, S. E., Madhoo, S., Soutar, A. K., Hawkins, P. N., Van Zyl-Smit, R., Campistol, J. M., Fraser, P. E., Radford, S. E., Robinson, C. V., Sunde, M., Serpell, L. C. and Blake, C. C. F. (1996) Molecular mechanisms of fibrillogenesis and the protective role of amyloid P component: two possible avenues for therapy. In: *The nature and origin of amyloid fibrils*, (Bock, G. R. and Goode, J. A., eds.), Wiley, Chichester (Ciba Foundation Symposium 199), pp. 7389.
4. Pepys, M. B., Booth, D. R., Hutchinson, W. L., Gallimore, J. R., Collins, P. M. and Hohenester, E. (1997) Amyloid P component. A critical review. *Amyloid. Int. J. Exp. Clin. Invest.*, 4: 274–295.
5. Pepys, M. B. (1999) The Lumleian Lecture. C-reactive protein and amyloidosis: from proteins to drugs? In: *Horizons in Medicine*, Vol. 10 (Williams, G., eds.), Royal College of Physicians, London, pp. 397–414.
6. Pepys, M. B., Dash, A. C., Munn, E. A., Feinstein, A., Skinner, M., Cohen, A. S., Gewurz, H., Osmand, A. P. and Painter, R. H. (1977) Isolation of amyloid P component (protein AP) from normal serum as a calcium-dependent binding protein. *Lancet*, i: 1029–1031.
7. Pontet, M., Engler, R. and Jayle, M. F. (1978) One step preparation of both human C-reactive protein and Clt. *Fed. Eur. Biol. Soc. Lett.*, 88: 172–178.
8. Hind, C. R. K., Collins, P. M., Renn, D., Cook, R. B., Caspi, D., Baltz, M. L. and Pepys, M. B. (1984) Binding specificity of serum amyloid P component for the pyruvate acetal of galactose. *J. Exp. Med.*, 159: 1058–1069.
9. Emsley, J., White, H. E., O'Hara, B. P., Oliva, G., Srinivasan, N., Tickle, I. J., Blundell, T. L., Pepys, M. B. and Wood, S. P. (1994) Structure of pentameric human serum amyloid P component. *Nature*, 367: 338–345.
10. Hohenester, E., Hutchinson, W. L., Pepys, M. B. and Wood, S. P. (1997) Crystal structure of a decameric complex of human serum amyloid P component with bound dAMP. *J. Mol. Biol.*, 269: 570–578.
11. Ashton, A. W., Boehm, M. K., Gallimore, J. R., Pepys, M. B. and Perkins, S. J. (1997) Pentameric and decameric structures in solution of serum amyloid P component by X-ray and neutron scattering and molecular modelling analyses. *J. Mol. Biol.*, 272: 408–422.
12. Baltz, M. L., de Beer, F. C., Feinstein, A. and Pepys, M. B. (1982) Calcium-dependent aggregation of human serum amyloid P component. *Biochim. Biophys. Acta*, 701: 229–236.
13. Booth, D. R., Gallimore, J. R., Hutchinson, W. L., Hohenester, E., Thompson, D., Wood, S. and Pepys, M. B. (1999) Analysis of autoaggregation and ligand binding sites of serum amyloid P component by in vitro mutagenesis. In: *Amyloid and Amyloidosis* 1998, (Kyle, R. A. and Gertz, M. A., eds.), Parthenon Publishing, Pearl River, N.Y., pp. 23–25.

14. Hutchinson, W. L., Hohenester, E. and Pepys, M. B. (2000) Human serum amyloid P component is a single uncomplexed pentamer in whole serum. *Mol. Med.*, 6:482493.
15. Hawkins, P. N., Wootton, R. and Pepys, M. B. (1990) Metabolic studies of radioiodinated serum amyloid P component in normal subjects and patients with systemic amyloidosis. *J. Clin. Invest.*, 86: 1862–1869.
16. Hutchinson, W. L., Noble, G. E., Hawkins, P. N. and Pepys, M. B. (1994) The pentraxins, C-reactive protein and serum amyloid P component, are cleared and catabolized by hepatocytes in vivo. *J. Clin. Invest.*, 94: 1390–1396.
17. Pepys, M. B., Rademacher, T. W., Amatayakul-Chantler, S., Williams, P., Noble, G. E., Hutchinson, W. L., Hawkins, P. N., Nelson, S. R., Gallimore, J. R., Herbert, J., Hutton, T. and Dwek, R. A. (1994) Human serum amyloid P component is an invariant constituent of amyloid deposits and has a uniquely homogeneous glycostructure. *Proc. Natl. Acad. Sci. USA*, 91: 5602–5606.
18. Holmgren, G., Steen, L., Ekstedt, J., Groth, C.-G., Ericzon, B.-G., Eriksson, S., Andersen, O., Karlberg, I., Norden, G., Nakazato, M., Hawkins, P., Richardson, S. and Pepys, M. (1991) Biochemical effect of liver transplantation in two Swedish patients with familial amyloidotic polyneuropathy (FAP-met[30]). *Clin. Genet.*, 40: 242–246.
19. Holmgren, G., Ericzon, B.-G., Groth, C.-G., Steen, L., Suhr, O., Andersen, O., Wallin, B. G., Seymour, A., Richardson, S., Hawkins, P. N. and Pepys, M. B. (1993) Clinical improvement and amyloid regression after liver transplantation in hereditary transthyretin amyloidosis. *Lancet*, 341: 1113–1116.
20. Klabunde, T., Petrassi, H. M., Oza, V. B., Raman, P., Kelly, J. W. and Sacchettini, J. C. (2000) Rational design of potent human transthyretin amyloid disease inhibitors. *Nature Struct. Biol.*, 7: 312–321.
21. Purkey, H. E., Dorrell, M. I. and Kelly, J. W. (2001) Evaluating the binding selectivity of transthyretin amyloid fibril inhibitors in blood plasma. *Proc. Natl. Acad. Sci. USA*, 98: 5566–5571.
22. Pepys, M. B., Hawkins, P. N., Booth, D. R., Vigushin, D. M., Tennent, G. A., Soutar, A. K., Totty, N., Nguyen, O., Blake, C. C. F., Terry, C. J., Feest, T. G., Zalin, A. M. and Hsuan, J. J. (1993) Human lysozyme gene mutations cause hereditary systemic amyloidosis. *Nature*, 362: 553–557.
23. Booth, D. R., Sunde, M., Bellotti, V., Robinson, C. V., Hutchinson, W. L., Fraser, P. E., Hawkins, P. N., Dobson, C. M., Radford, S. E., Blake, C. C. F. and Pepys, M. B. (1997) Instability, unfolding and aggregation of human lysozyme variants underlying amyloid fibrillogenesis. *Nature*, 385: 787–793.
24. Nelson, S. R., Tennent, G. A., Sethi, D., Gower, P. E., Ballardie, F. W., Amatayakul-Chantler, S. and Pepys, M. B. (1991) Serum amyloid P component in chronic renal failure and dialysis. *Clin. Chim. Acta*, 200: 191–200.

What is claimed is:

1. A method for the depletion of serum amyloid P component (SAP) from the plasma of a subject in need of such treatment, which comprises:
   (a) administering to the subject a therapeutically effective amount of a D-proline of the formula (R)-1-[6-[(R)-2-Carboxy-pyrrolidin-1-yl]-6-oxo-hexanoyl-]pyrrolidine-2-carboxylic acid or a pharmaceutically acceptable salt or mono- or diester thereof, wherein R is the group

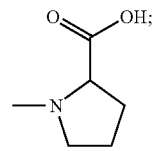

(b) binding of at least two ligands of said D-proline by ligand binding sites of SAP proteins in the plasma;
   (c) forming thereby a complex between said D-proline and a plurality of SAP proteins, wherein the complex is abnormal to the subject; and
   (d) causing the complex to be identified by the physiological mechanisms of the subject and cleared from the plasma; and
   (e) monitoring the clearance of SAP from the subject's plasma.

2. A method for the depletion of a SAP from the plasma of a subject in need of such treatment, which comprises administering to the subject a therapeutically effective amount of D-proline of the formula (R)-1-[6-(R)-2-Carboxy-pyrrolidin-1-yl]-6-oxo-hexanoyl] pyrrolidine-2-carboxylic acid or a pharmaceutically acceptable salt or mono- or diester thereof, wherein R is the group

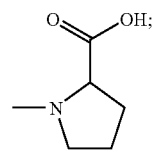

and monitoring the clearance of SAP from the subject's plasma.

3. The method of claim 1, wherein said D-proline is administered orally with a dosage of 50 to 500 mg/per day.
4. The method of claim 1, wherein said D-proline is administered by injection with a dosage of 0.05 to 6 mg/kg/day.
5. The method of claim 4, wherein said D-proline is administered by injection with a dosage of 0.1 to 6 mg/kg/day.
6. The method of claim 5, wherein said D-proline is administered by injection with a dosage of 0.25 to 6 mg/kg/day.
7. The method of claim 1, wherein said D-proline is administered orally with a dosage of 50 to 500 mg/per day.
8. The method of claim 1, wherein said D-proline is administered by injection with a dosage of 0.05 to 6 mg/kg/day.
9. The method of claim 8, wherein said D-proline is administered by injection with a dosage of 0.1 to 6 mg/kg/day.
10. The method of claim 9, wherein said D-proline is administered by injection with a dosage of 0.25 to 6 mg/kg/day.

* * * * *

UNITED STATES PATENT AND TRADEMARK OFFICE
CERTIFICATE OF CORRECTION

PATENT NO. : 7,045,499 B2  Page 1 of 1
APPLICATION NO. : 09/985699
DATED : May 16, 2006
INVENTOR(S) : Mark Pepys It is certified that error appears in the above-identified patent and that said Letters Patent is hereby corrected as shown below:

In the Abstract: Line 4, change "whierein" to --wherein--;
Line 6, change "non-protein access" to --non-proteinaceous--;

In the Specification: Column 2, line 22, change "(1-5) U.S. Patent No. 6,126,918)" to --(1-5; and U.S. Patent No. 6,126,918)--;
Column 15, line 14, change "R₃C" to --F₃C--.

In the Claims: Claim 1, which appears at column 20, lines 2-12, delete the expression: "wherein R is the group

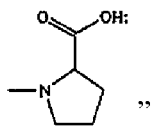

"

Claim 2, which appears at column 20, lines 29-38, delete the expression "wherein R is the group

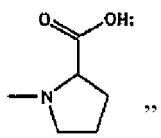

"

Signed and Sealed this

Sixteenth Day of October, 2007

JON W. DUDAS
*Director of the United States Patent and Trademark Office*